United States Patent
Shaw et al.

(10) Patent No.: US 9,487,497 B2
(45) Date of Patent: Nov. 8, 2016

(54) SYNTHETIC PROCESS FOR PREPARING 2-((2-ETHOXY-2-OXOETHYL)(METHYL) AMINO)-2-OXOETHYL 5-TETRADECYL-OXY)FURAN-2-CARBOXYLATE

(71) Applicant: Dermira Inc., Menlo Park, CA (US)

(72) Inventors: Anthony Adrian Shaw, Menlo Park, CA (US); Kanjai Khumtaveeporn, Aurora (CA); Pavel Krasik, Aurora (CA)

(73) Assignee: DERMIRA INC., Menlo Park, CA (US)

(*) Notice: Subject to any disclaimer, the term of this patent is extended or adjusted under 35 U.S.C. 154(b) by 0 days.

(21) Appl. No.: 15/015,828

(22) Filed: Feb. 4, 2016

(65) Prior Publication Data

US 2016/0229826 A1 Aug. 11, 2016

Related U.S. Application Data

(60) Provisional application No. 62/112,569, filed on Feb. 5, 2015.

(51) Int. Cl.
| | |
|---|---|
| *A61K 31/55* | (2006.01) |
| *C07D 307/68* | (2006.01) |
| *C07D 307/56* | (2006.01) |

(52) U.S. Cl.
CPC .......... *C07D 307/68* (2013.01); *C07D 307/56* (2013.01)

(58) Field of Classification Search
None
See application file for complete search history.

(56) References Cited

U.S. PATENT DOCUMENTS 8,884,034 B2 11/2014 Daynard et al.

OTHER PUBLICATIONS

Parker et al., "5-(Tetradecyloxy)-2-furancarboxylic Acid and Related Hypolipidemic Fatty Acid-Like Alkyloxyarylcarboxylic Acids," *Journal of Medicinal Chemistry* 20(6):781-791, 1977.

*Primary Examiner* — Heidi Reese
(74) *Attorney, Agent, or Firm* — Seed IP Law Group LLP

(57) ABSTRACT

Disclosed herein are processes for forming 2-((2-ethoxy-2-oxoethyl)(methyl)amino)-2-oxoethyl 5-tetradecyloxy)furan-2-carboxylate:

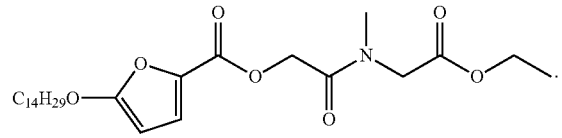

18 Claims, No Drawings

SYNTHETIC PROCESS FOR PREPARING 2-((2-ETHOXY-2-OXOETHYL)(METHYL) AMINO)-2-OXOETHYL 5-TETRADECYL-OXY)FURAN-2-CARBOXYLATE

CROSS-REFERENCES TO RELATED APPLICATION

This application claims the benefit under 35 U.S.C. §119 (e) of U.S. Provisional Patent Application No. 62/112,569, filed Feb. 5, 2015, which application is incorporated herein by reference in its entirety.

BACKGROUND

1. Technical Field

This disclosure is generally related to a synthetic process for preparing 2-((2-ethoxy-2-oxoethyl)(methyl)amino)-2-oxoethyl 5-tetradecyloxy)furan-2-carboxylate, a prodrug of a fatty acid mimetic.

2. Background

Fatty acid synthesis starts with the carboxylation of acetyl CoA to malonyl CoA. This irreversible reaction is the committed step in fatty acid synthesis.

The synthesis of malonyl CoA is catalyzed by acetyl CoA carboxylase (ACC) (See, Brownsey, R. W. et al., "Regulation of acetyl-CoA carboxylase", *Biochem Soc. Trans.* (2006) 34: 223-227).

Inhibition of ACC can be effective in diminishing fatty acid synthesis. Long-chain (16-20 carbons) fatty acid acyl-CoA thioesters have been found to be potent physiological end-product inhibitors of mammalian ACC.

TOFA (5-(tetradecyloxy)-2-furoic acid) is a known fatty acid mimetic, which can be converted intracellularly to its acyl-CoA thioester, thus inhibiting ACC activity with a mechanism similar to long chain fatty acid acyl-CoA thioesters. See, McCune, S. A. et al., *J. Biol. Chem.* (1979), Vol. 254, No. 20, pp. 10095-10101.

TOFA has the following structure:

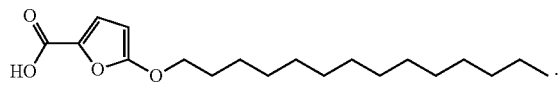 [SMILES: CCCCCCCCCCCCCCOc1ccc(C(=O)O)o1]

TOFA has been shown to reduce plasma triglyceride levels in both rats and monkeys. See, e.g., Parker, R. A. et al., *J. Med. Chem.* (1977), Vol. 20, pp. 781-791. It has also been known to inhibit hepatic fatty acid synthesis. See, e.g., Ribereau-Gayon, G., *FEBS Lett.* (1976), Vol. 62, No. 309-312; Panek, E. et al., *Lipids* (1977), Vol. 12, pp. 814-818; Kariya, T. et al., *Biochem. Biophys. Res. Commun.* (1978), Vol. 80, pp. 1022-1024; and Harris, R. A. et al., *Hormones and Energy Metabolism* (Klachko, D. M. et al., eds.), Vol. III, pp. 17-42. TOFA is further known to inhibit sebaceous gland disorders by lowering sebum production. See, e.g., U.S. Published Patent No. 2010/0204317, and German Patent No. 40 33 563.

TOFA has poor bioavailability through the skin. On the other hand, certain TOFA prodrugs have been found to be particularly effective against a range of dermatological disorders including acne vulgaris, acne conglobata, choracne, rosacea, Rhinophyma-type rosacea, seborrhea, seborrheic dermatitis, sebaceous gland hyperplasia, Meibomian gland dysfunction of facial rosacea, mitogenic alopecia, and oily skin. See U.S. Pat. No. 8,884,034, in the name of Dermira (Canada) Inc.

One such TOFA prodrug is 2-((2-ethoxy-2-oxoethyl) (methyl)amino)-2-oxoethyl 5-tetradecyloxy)furan-2-carboxylate, having the following structure:

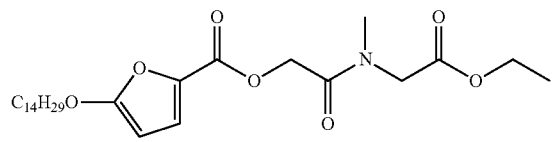

There is a need to modify the synthetic approach to produce TOFA prodrugs at improved yields and scalability.

BRIEF SUMMARY

One embodiment provides a process for preparing a compound of Formula (I)

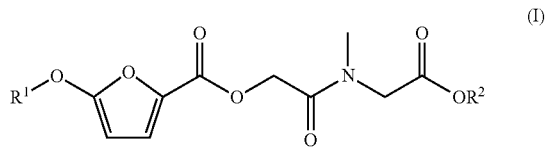

comprising:

providing a compound of Formula (II) combined with a first solvent; and

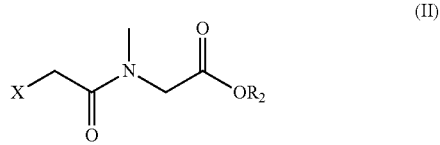

coupling the compound of Formula (II) with a compound of Formula (III) in a second solvent,

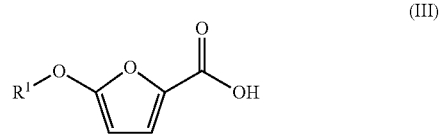

wherein, $R^1$ is $C_{10-20}$ alkyl;

$R^2$ is $C_{1-4}$ alkyl;

X is a leaving group; and the first solvent is an ether solvent and is the same as the second solvent.

In another embodiment, providing the compound of Formula (II) combined with the first solvent comprises coupling a compound of Formula (IV) with X—$CH_2$—C(O)Cl in the first solvent, wherein Formula (IV) has the following structures:

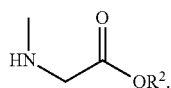

(IV)

In a further embodiment, the coupling of the compound of Formula (II) with the compound of Formula (III) is carried out in the presence of an organic base.

DETAILED DESCRIPTION

Described herein includes a process for preparing a compound represented by Formula (I):

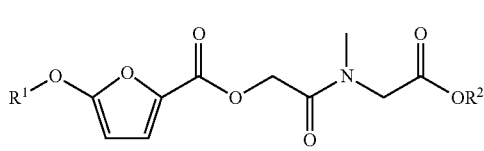

(I)

comprising:
providing a compound of Formula (II) combined with a first solvent; and

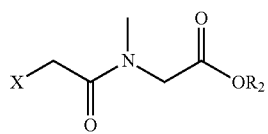

(II)

coupling the compound of Formula (II) with a compound of Formula (III) in a second solvent,

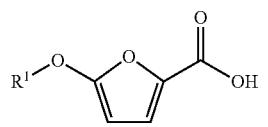

(III)

wherein,
$R^1$ is $C_{10-20}$ alkyl;
$R^2$ is $C_{1-4}$ alkyl;
X is a leaving group; and
the first solvent is an ether solvent and is the same as the second solvent.

In various further embodiments, X is a halogen (e.g., Cl, Br or I).

In various further embodiments, the first solvent and the second solvent are dialkyl ether. In other further embodiments, the ether has a boiling point of below 100° C.

The first reactant, a compound of Formula (II), may be prepared by known methods in the art, including for example, the Schotten-Baumann reaction:

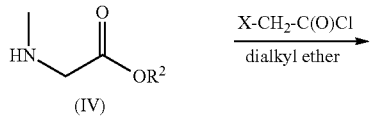

(IV)

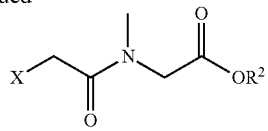

(II)

The second reactant, a compound of Formula (III), is commercially available (e.g., TOFA) or may be prepared by known methods in the art. See Parker, R. A. et al., (Supra). It may also be prepared by the method described in co-pending U.S. patent application Ser. No. 15/015,569, in the name of Dermira Inc., which application is incorporated herein by reference in its entirety.

In certain embodiments, prior to the coupling reaction, the reactants are separately present in the same type of ether solvent (e.g., dialkyl ether). Advantageously, the reactant of Formula (II) may be prepared in the same ether solvent as well, and be used directly in the coupling reaction with the reactant of Formula (III) in the presence of a suitable base (e.g., an organic base). Suitable organic bases include, without limitation, trialkylamine (e.g., trimethylamine or triethylamine) or dialkylamine (e.g., dimethylamine) and the like.

As used herein, "alkyl" refers to a straight or branched hydrocarbon chain radical consisting solely of carbon and hydrogen atoms, containing no unsaturation, having from one to twenty four carbon atoms ($C_{1-24}$ alkyl). Long-chain alkyls include, for example, ten to twenty carbon atoms ($C_{10-20}$ alkyl), or ten to fifteen carbon atoms ($C_{10-15}$ alkyl). Short-chain alkyls include, for example, one to eight carbon atoms ($C_{1-8}$ alkyl), or one to six carbon atoms ($C_{1-6}$ alkyl), or one to four carbon atoms ($C_{1-4}$ alkyl). The alkyl radical is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be unsubstituted or substituted by halo (F, Cl, Br, or I), haloalkyl (e.g., $CF_3$), alkoxy (i.e., —O-alkyl), hydroxy (—OH), acyl group (—OC(O)alkyl) or carboxyl group.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene.

"Ether" refers to a compound having two alkyl or aryl groups bonded to an oxygen. "Dialkyl ether" refers to a compound represented by alkyl-O-alkyl, in which the alkyl group is as defined here, and may be the same or different.

As used herein, suitable dialkyl ether solvents typically have low boiling points (i.e., below 100° C.), more preferably, the boiling point is below 60° C. Examples of the suitable dialkyl ether solvent include methyl t-butyl ether (MTBE), which has a boiling point of 55° C.

"Leaving group" refers to a molecular fragment that is capable of being displaced (e.g., in a SN2 reaction) by a nucleophile. For example, a leaving group may be a halogen (i.e., Br, Cl or I), or a tosyl group (e.g., -OTs).

In preferred embodiments, $R^1$ is —$C_{14}H_{29}$.

In various embodiments, $R^2$ is ethyl.

In preferred embodiments, X is Cl.

Example 2-((2-ethoxy-2-oxoethyl)(methyl)amino)-2-oxoethyl 5-tetradecyloxy)furan-2-carboxylate was prepared according to the following scheme of 0.307 g (2.0 mmol) of sarcosine ethyl ester hydrochloride (1) in EtOAc (3 mL) and 3 mL of saturated $NaHCO_3$ solution was added chloroacetyl chloride (3) (0.160 mL, 2 mmol). Effervescence was observed. Once gas production had ceased, the reaction mixture was diluted with ethyl acetate (10 mL). The phases were separated and the organic phase was washed with brine (5 mL), dried and concentrated to yield ~0.250 g of the title compound (2) as an oil. The crude material was used in the subsequent step without further purification.

The above processes were shown to be scalable with minor changes. An output scale of 13 kg (corrected for purity) with yields varying from 60-80% could be consistently obtained.

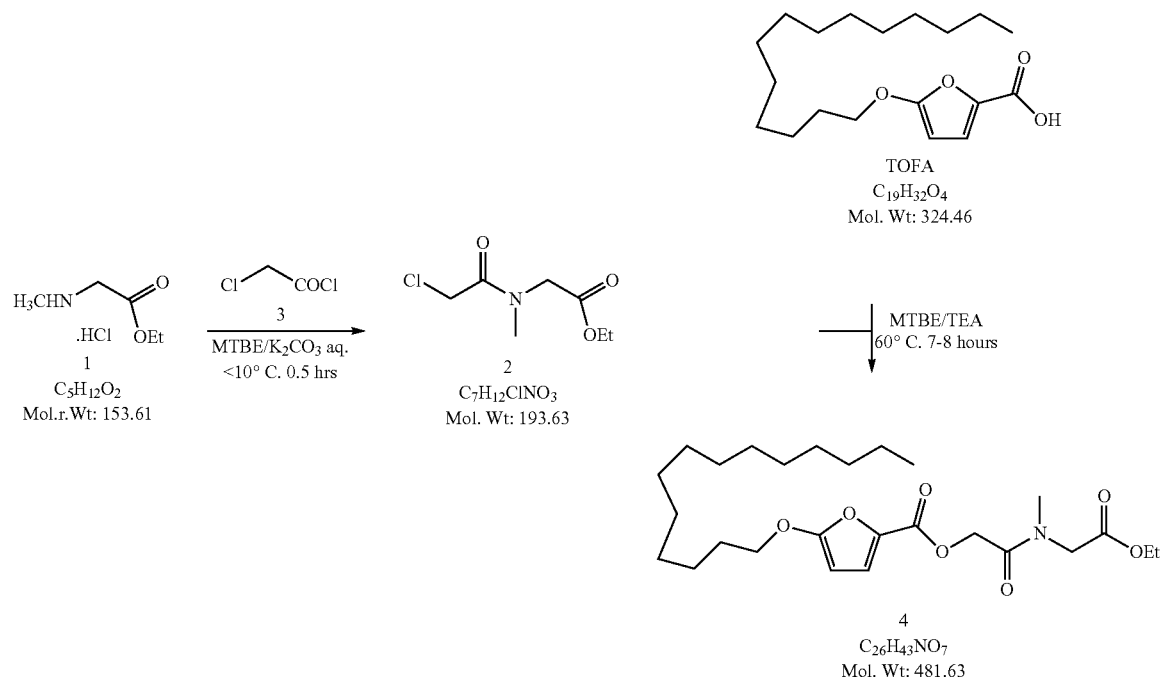

Step 1: Preparation of 2—a compound of Formula (II)

Compound (2) was prepared by acylation of Compound (1) under Schotten-Baumann conditions. More specifically, an aqueous solution of potassium carbonate and chloroacetyl chloride (3) was added to a vigorously stirred suspension of sarcosine ethyl ester hydrochloride (1) in a dialkyl ether (e.g., MTBE). The reaction proceeded quantitatively at ambient temperature within about 30 minutes. The crude reaction mixture can be optionally diluted with the dialkyl ether solvent (MTBE), and underwent phase separation. After the aqueous phase was removed, the title compound (2), which was present in the organic layer (i.e. MTBE), could be used directly for the coupling step (Step 2).

The Schotten-Baumann conditions could also be slightly modified to produce compound (2) as follows. To a mixture Step 2—Coupling of (2) and TOFA The coupling reaction was conducted over 7-8 hours in MTBE under reflux (~60° C.) in the presence of a suitable base such as triethylamine (TEA). After aqueous work-up using a phosphate buffer, the organic phase underwent solvent exchange to 2-propanol. Crystallization of the coupling product (4) was induced by addition of water and was isolated at about 83% yield from TOFA. Advantageously, because the same solvent (MTBE) could be used in both Steps, the top volume of the claimed process could be less than half that of the conventional process, thereby significantly improving throughput.

All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

The invention claimed is:

1. A process for preparing a compound of Formula (I)

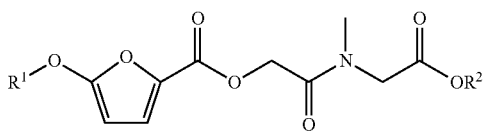

comprising:
  providing a compound of Formula (II) combined with a first solvent; and

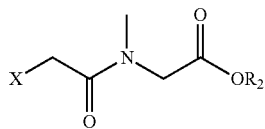

coupling the compound of Formula (II) with a compound of Formula (III) in a second solvent,

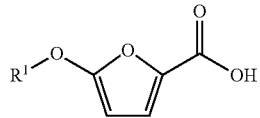

wherein,
  $R^1$ is $C_{10-20}$ alkyl;
  $R^2$ is $C_{1-4}$ alkyl;
  X is a leaving group; and
  the first solvent is an ether solvent and is the same as the second solvent.

2. The process of claim 1 wherein X is halogen.

3. The process of claim 2 wherein X is Cl.

4. The process of claim 1 wherein the ether solvent is dialkyl ether.

5. The process of 1 wherein the ether solvent has a boiling point of below 100° C.

6. The process of claim 5 wherein the first solvent and the second solvent are methyl t-butyl ether.

7. The process of claim 1 wherein $R^1$ is —$C_{14}H_{29}$.

8. The process of claim 1 wherein $R^2$ is ethyl.

9. The process of claim 1 wherein the compound of Formula (I) is 2-((2-ethoxy-2-oxoethyl)(methyl)amino)-2-oxoethyl 5-tetradecyloxy)furan-2-carboxylate.

10. The process of claim 1 wherein providing the compound of Formula (II) combined with the first solvent comprises coupling a compound of Formula (IV) with X—$CH_2$—C(O)Cl in the first solvent, wherein Formula (IV) has the following structures:

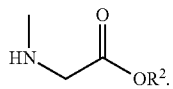

11. The process of claim 10 wherein the first solvent is an ether solvent having a boiling point of below 100° C.

12. The process of claim 11 wherein the first solvent is methyl t-butyl ether.

13. The process of claim 10 wherein $R^2$ is ethyl.

14. The process of claim 10 wherein X is halogen.

15. The process of claim 14 wherein X is Cl.

16. The process of claim 1 wherein the coupling of the compound of Formula (II) with the compound of Formula (III) is carried out in the presence of an organic base.

17. The process of claim 16 wherein the organic base is trialkylamine.

18. The process of claim 17 wherein the organic base is triethylamine.

* * * * *